Feb. 14, 1950 T. J. MORRIS Plant Pat. 923
ROSE PLANT
Filed Aug. 30, 1948
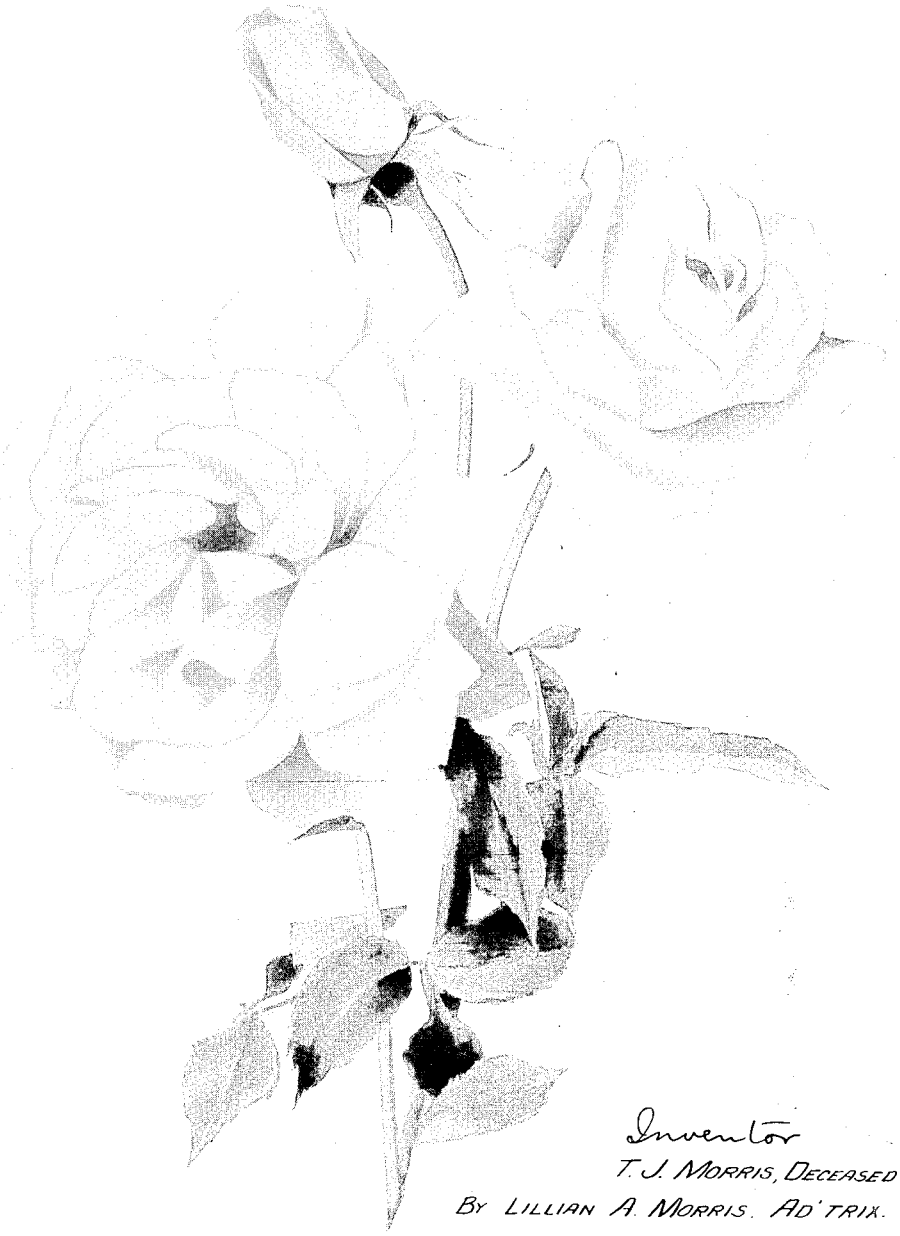
Inventor
T. J. MORRIS, DECEASED
BY LILLIAN A. MORRIS, AD'TRIX.
By Robb & Robb
Attorneys Patented Feb. 14, 1950 Plant Pat. 923

UNITED STATES PATENT OFFICE

923

ROSE PLANT

Theodore John Morris, deceased, late of Van Nuys, Calif., by Lillian Adelle Morris, administratrix, Van Nuys, Calif., assignor to Germain's Inc., Van Nuys, Calif., a corporation of California Application August 30, 1948, Serial No. 46,862

1 Claim. (Cl. 47—61)

The present invention relates to a new and distinct variety of rose plant characterized by its exceptional free-blooming and vigorous branching habits of growth, its relative freedom from thorns, the distinctive color of its blossoms, and its ease of propagation.

This new variety most nearly resembles its seed parent but differs dominantly therefrom in respect of the color of the blooms; that is, the present variety belongs to the vermilion color range rather than to the copper-orange of its seed parent. This variety also is a much more prolific bloomer, has much more vigor of growth, and is freer flowering than its parents.

Asexual reproduction of this new variety shows the foregoing characteristics come true to form and are established.

In the accompanying drawings are illustrated specimens of this new rose at different states of development of the flowers.

The following is a detailed description of the new variety, color terminology being in accordance with the Royal Horticultural Society Color Chart, except where otherwise indicated to have ordinary dictionary significance:

Type: Half-hardy; bush; outdoor; seedling; for cut flowers and garden decoration.
Class: Hybrid tea.
Breeding:
*Seed parent.*—"Mrs. Sam McGredy" (unpatented).
*Pollen parent.*—"Malar Ros" (unpatented).
Propagation: Holds its distinguishing characteristics through succeeding propagations by cuttings, grafting and budding.

*Flower*

Locality where grown: Van Nuys, California.
Flowers borne: Singly to stem; on normal strength, medium length stems.
Quantity of bloom: Abundant; outdoors.
Continuity: Continuous.
Fragrance: Moderate; sweetbriar.
Bud:
*Peduncle.*—Long; medium erect; light reddish green; entirely smooth.
*Before calyx breaks.* — Size — medium. Form—long; pointed, with a conspicuous neck; without foliaceous appendages on the surface of the bud; with much cut foliaceous parts extending beyond the tip of the bud equal to one-half or more of its length. Color—light green.
*As calyx breaks.*—Color—Jasper Red, Plate o18.

*As first petal opens.*—Size—medium. Form—pointed. Color—outside: Jasper Red, Plate o18/2; inside: Geranium Lake, Plate 20/1.
*Opening.*—Opens up well.
Bloom: Size, when fully open—medium; 5 inches to 5½ inches.
*Petalage.*—Double; from 40 to 45 petals arranged irregularly.
*Form.*—Full at first; becoming high centered; petals at first loosely rolled outward and remaining loosely rolled outward.
Petals: Thick; leathery; with inside satiny and outside shiny.
*Shape.*—Outside—obovate. Intermediate—obovate. Inside—obovate; linear.

This description of a newly opened flower was made from a rose grown outdoors in the month of June at Van Nuys, California:

*Color.—Outside petal*—outside surface—Vermilion, Plate 18/2; inside surface—Claret Rose, Plate o21/1. *Intermediate petal*—outside surface—Vermilion, Plate 18/2; inside surface—Claret Rose, Plate o21/1. *Inner petal*—outside surface—Claret Rose, Plate o21/2; inside surface—Vermilion, Plate 18/2.

This description was made from a rose that was open for three days outdoors in the month of June, at Van Nuys, California:

*Color. — Outside petal* — outside surface—Spinel Pink, Plate o625/2; inside surface—Spinel Pink, Plate o625/1. *Inner petal*—outside surface—Spinel Pink, Plate o625/2; inside surface—Spinel Pink, Plate o625/1.
*General color effect.*—Newly opened flower—Claret Rose, Plate o21/1. Three days open—Spinel Pink, Plate o625/1.
*Behavior.*—Persist; brown.
*Flower longevity.*—On bush in garden—4 days in June. Cut roses grown outdoors, kept at living room temperature—3 days in June.

*Reproductive organs*

Stamens: Many; arranged regularly about pistils.
Filaments: Long; yellow; most with anthers.
Anthers: Medium size; yellow; all open at once.
Pollen: Moderate; yellow.
Pistils: Medium number.
Styles: Uneven; medium long; thin; loosely bunched.

Stigma: Red.
Ovaries: All enclosed in calyx.
Hips: Long; gourd-shaped; green; smooth; thin.
Sepals: Permanent; long; recurved; green.
Seeds: Many; medium size.

*Plant*

Foliage: Leaves, compound of five leaflets; abundant; medium size; moderately thin; soft.
*Leaflets.*—Mucronate; base round; margin irregularly serrate.
*Color.* — *Mature* — upper surface — Dark Green; under surface—Light Grey Green.
*Rachis.* — Medium heavy; upper side — grooved; under side—sparsely prickly.
*Stipules.*—Medium length; medium width; with medium points turning out at an angle of less than 90°, recurved toward the stem.
*Disease.*—Subject to mildew.
Growth:
*Habit.*—Bushy; much branched.
*Growth.*—Vigorous.
*Canes.*—Medium heavy.

*Main stems.*—Dull green. *Thorns*—few; medium long; straight; with long narrow base. *Prickles*—none. *Hairs*—none.
*Branches.*—Dull green. *Thorns*—few; medium long; hooked downward; with long narrow base. *Prickles*—none. *Hairs*—none.
*New shoots.*—Dull red. *Thorns*—very few; medium long; hooked downward; with long narrow base. *Prickles* — none. *Hairs*—none.

It is claimed:

A new and distinct variety of hybrid tea rose plant characterized as to novelty by its exceptional free-blooming habit; its vigorous branching habit of growth; its relative freedom from thorns; its ease of propagation; and the distinctive color of its flowers, substantially as shown and described.

LILLIAN ADELLE MORRIS,
*Administratrix of the Estate of Theodore John Morris, Deceased.*

No references cited.